United States Patent
Damm et al.

(10) Patent No.: US 11,833,033 B2
(45) Date of Patent: Dec. 5, 2023

(54) INJECTOR ASSEMBLY FOR INSERTING AN INTRAOCULAR LENS AND INJECTOR

(71) Applicant: CARL ZEISS MEDITEC AG, Jena (DE)

(72) Inventors: Niklas Damm, Berlin (DE); Jakob Jastram, Berlin (DE); Alfred Rinman, Hamburg (DE)

(73) Assignee: CARL ZEISS MEDITEC AG, Jena (DE)

( * ) Notice: Subject to any disclaimer, the term of this patent is extended or adjusted under 35 U.S.C. 154(b) by 0 days.

(21) Appl. No.: 18/001,387

(22) PCT Filed: Jun. 7, 2021

(86) PCT No.: PCT/EP2021/065173
§ 371 (c)(1),
(2) Date: Dec. 9, 2022

(87) PCT Pub. No.: WO2021/249944
PCT Pub. Date: Dec. 16, 2021

(65) Prior Publication Data
US 2023/0190455 A1 Jun. 22, 2023

(30) Foreign Application Priority Data
Jun. 10, 2020 (DE) .................... 10 2020 115 489.5

(51) Int. Cl.
*A61F 2/16* (2006.01)
(52) U.S. Cl.
CPC ............ *A61F 2/1678* (2013.01); *A61F 2/167* (2013.01)
(58) Field of Classification Search
CPC .................. A61F 2/1678; A61F 2/167; A61F 2002/1681; A61F 2002/1682;
(Continued)

(56) References Cited

U.S. PATENT DOCUMENTS

2008/0033449 A1 2/2008 Cole et al.
2014/0135784 A1* 5/2014 Maroscheck ......... A61F 2/1678
606/107
(Continued)

FOREIGN PATENT DOCUMENTS

AU 2016244314 B2 11/2016
CN 104127264 A 11/2014
(Continued)

OTHER PUBLICATIONS

Written Opinion of the International Searching Authority for PCT/EP2021/065173 (ISA/CN) dated Sep. 14, 2021 (5 pages).
(Continued)

*Primary Examiner* — Ashley L Fishback
*Assistant Examiner* — Chima U Igboko
(74) *Attorney, Agent, or Firm* — ALSTON & BIRD LLP

(57) ABSTRACT

The invention relates to an injector assembly having: a folding chamber which is designed to receive an intraocular lens which has an optical body and two haptic elements; a holder; a folding wedge which is attached to the holder and is designed to be introduced into the folding chamber via a folding chamber opening, thereby folding the intraocular lens; and a first slider and a second slider which are each designed to push one of the two haptic elements onto the optical body by means of a displacement of the respective slider from a starting position to an end position, the holder being designed to drive the first slider and/or the second slider from the starting position to the end position by means of a movement of the holder towards the folding chamber.

9 Claims, 4 Drawing Sheets

(58) Field of Classification Search
CPC .. A61F 2002/16903; A61F 2002/16905; A61F 2002/169052; A61F 2002/169053
See application file for complete search history.

(56) References Cited

U.S. PATENT DOCUMENTS

| | | |
|---|---|---|
| 2016/0270907 A1 | 9/2016 | Attinger |
| 2016/0331587 A1 | 11/2016 | Yamada et al. |
| 2019/0117381 A1 | 4/2019 | Maroscheck et al. |
| 2019/0254812 A1 | 8/2019 | Maroschek |
| 2020/0015958 A1 | 1/2020 | Zacher et al. |
| 2020/0197169 A1* | 6/2020 | Wu .................. A61F 2/167 |

FOREIGN PATENT DOCUMENTS

| | | |
|---|---|---|
| CN | 109640886 A | 4/2019 |
| DE | 10 2006 000 929 A1 | 7/2007 |
| EP | 2 408 398 B1 | 6/2014 |
| WO | WO 2012/155887 A1 | 11/2012 |
| WO | WO 2019/200336 A1 | 10/2019 |

OTHER PUBLICATIONS

German Office Action for 10 2020 115 489.5 dated Apr. 12, 2021.
International Search Report and Written Opinion for PCT/EP2021/065173 dated Sep. 14, 2021 (17 pages).
Office Action received for Chinese Patent Application No. 2021800417003, dated Jul. 14, 2023, 12 pages.

* cited by examiner

INJECTOR ASSEMBLY FOR INSERTING AN INTRAOCULAR LENS AND INJECTOR

CROSS-REFERENCE TO RELATED APPLICATIONS

The present application is a national phase entry of International Application No. PCT/EP2021/065173, filed Jun. 7, 2021, which claims priority to German Patent Application No. 10 2020 115 489.5, filed Jun. 10, 2020, which are each incorporated herein by reference in their entirety.

The invention relates to an injector assembly for inserting an intraocular lens into the capsular bag of an eye, and to an ophthalmosurgical injector having the injector assembly.

In cataract treatment of an eye, only a small incision is usually made in the cornea of the eye, said incision being large enough to allow a cannula of an injector to be inserted through the incision into the eye. After the incision has been made in the cornea, the lens of the eye is broken up by phacoemulsification and then sucked out of the capsular bag of the eye. Thereafter, an intraocular lens is inserted into the eye by means of the injector. The intraocular lens is folded inside the injector to fit through the cannula. The cannula is inserted into the capsular bag through the incision, and the folded intraocular lens is pushed by the injector through the cannula into the capsular bag, in which the intraocular lens unfolds and thus replaces the original lens. Errors may occur while the intraocular lens is being folded or while the folded intraocular lens is being pushed into the capsular bag. The errors can lead, for example, to the intraocular lens not fully unfolding in the capsular bag or to the intraocular lens even being damaged.

It is therefore the object of the invention to provide an injector assembly with which there is a low probability of errors occurring during use of the injector assembly.

The object is achieved by an injector assembly as claimed in independent claim 1. Advantageous developments of the invention are the subject matter of the dependent claims.

The injector assembly according to the invention has: a folding chamber which is designed to accommodate an intraocular lens comprising an optics body and two haptics, a holder, a folding wedge, which is attached to the holder and is designed to be introduced into the folding chamber via a folding chamber opening and thereby to fold the intraocular lens, and a first slider and a second slider which are each designed to displace one of the two haptics onto the optics body by displacement of the respective slider from a starting position into an end position, wherein the holder is designed to drive the first slider and/or the second slider from the starting position into the end position by movement of the holder toward the folding chamber.

By the two haptics being arranged on the optics body by means of the sliders, the haptics are arranged inside the optics body when the intraocular lens is folded by the folding wedge. As a result, the intraocular lens can be introduced into the capsular bag of an eye in a low-error and reproducible manner and the intraocular lens can be unfolded in the capsular bag in a low-error and reproducible manner. By the holder driving the first slider and/or the second slider into the end position, it is possible to avoid the folding wedge being introduced into the folding chamber before the first slider and/or the second slider has been brought into the end position and the haptics associated with the at least one slider have therefore been pushed onto the optics body. As a result, the injector assembly is particularly low in errors. The injector assembly is particularly low in errors when the holder is designed to drive both the first slider and the second slider from the starting position into the end position by movement of the holder toward the folding chamber.

The injector assembly preferably has an injector body, inside which the folding chamber is arranged, and a joint by means of which the holder is attached pivotably to the injector body. The holder is thus pivotable relative to the injector body, and the folding wedge is introduced into the folding chamber by pivoting the holder about the joint in the direction of the optics body.

It is preferred that the injector assembly has a pusher which is fastened to the first slider and extends from the first slider toward the joint, wherein the holder is designed to drive the pusher, by means of pivoting of the holder about the joint in the direction of the folding chamber, which thereby displaces the first slider into the end position. It is conceivable for the holder or a component fastened to the holder to contact the pusher during the pivoting and thus to drive the pusher.

Alternatively, it is preferred that the injector assembly has a first protrusion which is fastened to the holder and has a first sliding surface which is designed to slide along the first slider, when the holder is pivoted about the joint in the direction of the folding chamber, and thereby to displace the first slider into the final position. It is particularly preferred that the injector assembly has a second protrusion which is fastened to the holder and has a second sliding surface which is designed to slide along the second slider, when the holder is pivoted about the joint in the direction of the folding chamber, and thereby to displace the second slider into the final position.

It is preferred that the first slider has a first slider protrusion which protrudes from a side of the first slider facing away from the second slider and on which the first sliding surface is designed to slide, and/or that the second slider has a second slider protrusion which protrudes from a side of the second slider facing away from the first slider and on which the second sliding surface is designed to slide. The first sliding surface and/or the second sliding surface are preferably curved.

It is preferred that the injector assembly has a wheel which is designed to displace the first slider from the starting position into the end position by rotation of the wheel, and the holder is designed to set the wheel in rotation by means of pivoting the holder about the joint toward the folding chamber. The wheel is particularly preferably designed to displace the second slider from the starting position into the end position as a result of the rotation.

It is preferred that the injector assembly has a first rod, by means of which the wheel is coupled to the first slider to drive the first slider, and/or has a second rod, by means of which the wheel is coupled to the second slider to drive the second slider.

It is preferred that the joint has a pin which rotates upon pivoting of the holder and to which a first gearwheel is fastened, and the wheel is a second gearwheel, the teeth of which mesh with the teeth of the first gearwheel. Owing to the first gearwheel being fastened to the pin, the first gearwheel rotates when the holder is pivoted together with the pin. By means of the engagement of the teeth of the first gearwheel and the teeth of the second gearwheel, the first gearwheel drives the second gearwheel. It is conceivable that the axis of rotation of the first gearwheel is arranged substantially perpendicular to the axis of rotation of the second gearwheel. In addition, the axis of rotation of the first gearwheel can coincide with the axis of rotation of the pin.

The injector assembly preferably has the intraocular lens. Particularly preferably, the intraocular lens is arranged in the folding chamber.

The ophthalmosurgical injector according to the invention has the injector assembly.

The invention is explained in more detail below with reference to the accompanying schematic drawing.

Figure 1:
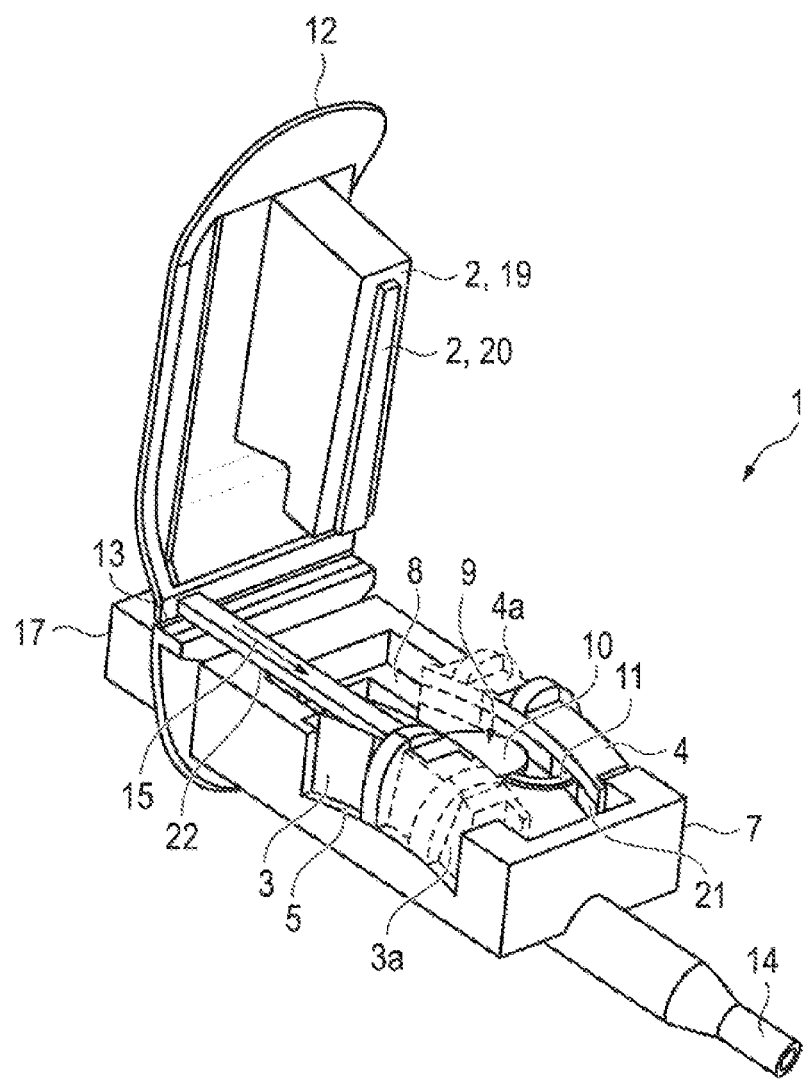
FIG. 1 shows a perspective view of a first embodiment of the injector assembly according to the invention with a first slider, which is shown both in the starting position and in the end position.

As can be seen from FIGS. 1 to 6, an injector assembly 1 has: a folding chamber 8 which is designed to accommodate an intraocular lens 9 comprising an optics body 10 and two haptics 11, a holder 12, a folding wedge 2, which is attached to the holder 12 and is designed to be introduced into the folding chamber 8 via a folding chamber opening 18 and thereby to fold the intraocular lens 9, and a first slider 3 and a second slider 4 which are each designed to displace one of the two haptics 11 onto the optics body 10 by displacement of the respective slider 3, 4 from a starting position into an end position, wherein the holder 12 is designed to drive the first slider 3 and/or the second slider 4 from the starting position into the end position by means of movement of the holder 12 toward the folding chamber 8.

Figure 6:
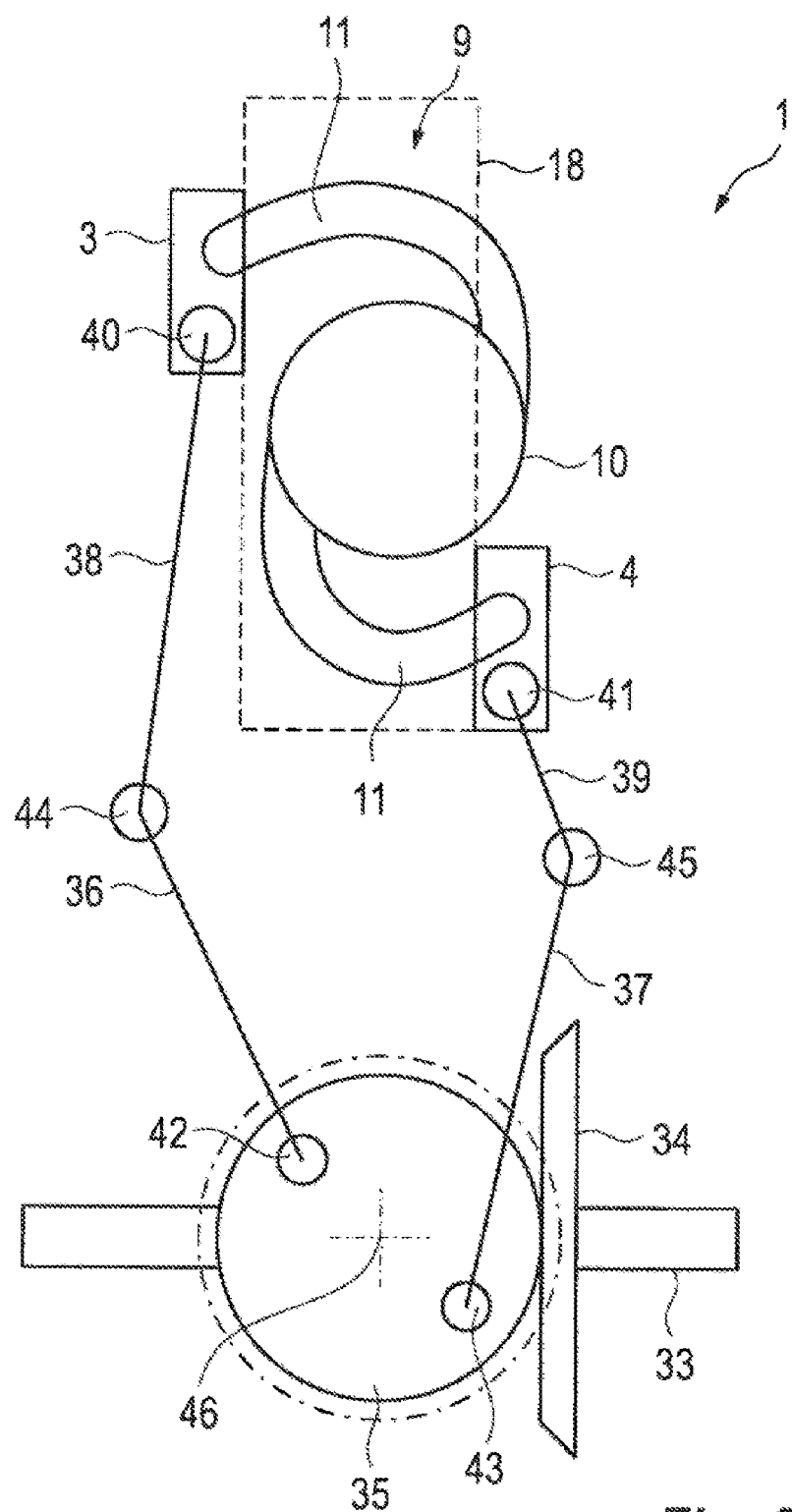
FIG. 6 shows a top view of a fourth embodiment of the injector assembly according to the invention with a first slide and a second slide, which are shown in a starting position.

The injector assembly 1 can have the intraocular lens 9. It is conceivable that the intraocular lens 1 is arranged in the folding chamber 8. FIGS. 1 and 6 show that the two haptics 11 can each be C-shaped.

FIGS. 1 and 6 show that the first slider 3 and the second slider 4 can be arranged at ends of the folding chamber 8 that face away from each other. In particular, the first slider 3 and the second slider 4 can be arranged at ends of the folding chamber opening 18 that face away from each other. The ends can be arranged facing away from each other in a direction perpendicular to a displacement direction in which the intraocular lens 9 can be displaced from the folding chamber 8 to a cannula 14 of the injector assembly 1. It can also be seen that the injector assembly 1 can have a first slider track 5 on which the first slider 3 is slidingly mounted and a second slider track (not shown) on which the second slider 4 is slidingly mounted. The first slider track 5 and the second slider track can be curved such that the sliders 3, 4 cover a curved path when they are displaced from the starting position into the end position. As a result, a collision of the haptics 11 with the peripheral edge of the optics body 10 can be avoided when the haptics 11 are displaced. It can be seen from FIG. 1 that the sliders 3, 4 can each have a slider pin 21 which protrudes from the slider 3, 4 in the direction of the intraocular lens 9. Each of the slider pins 21 is designed to grip one of the two haptics 11 and to displace it onto the optics body 10 when the slider 3, 4 associated with the slider pin 21 is displaced from the starting position into the end position. The slider pins 21 can protrude from a side of the slider 3, 4 which is arranged facing away from the folding wedge 2 arranged outside the folding chamber 8. This ensures that the haptics 11 are displaced to that side of the optics body 10 which faces the folding wedge 2. The effect which can be achieved by this is that the haptics 11 are arranged within the optics body 10 when the folding wedge 2 folds the intraocular lens 9.

FIGS. 1 to 4 show that the injector assembly 1 can have an injector body 7, inside which the folding chamber 8 is arranged, and a joint 13, by means of which the holder 12 is pivotably attached to the injector body 7. By pivoting of the holder 12 about the joint 13 in the direction of the injector body 7, the folding wedge 2 can be introduced into the folding chamber 8 and the intraocular lens 9 can thereby be folded.

Figure 2:
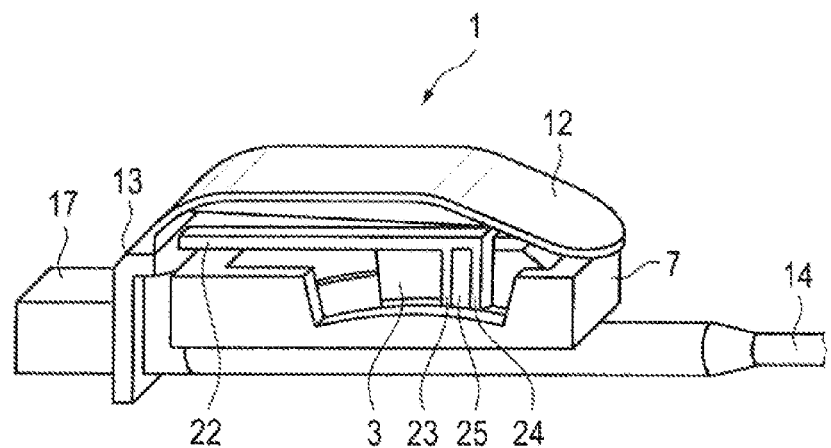
FIG. 2 shows a side view of the first embodiment with the first slider, which is shown in the end position.

For example, FIGS. 1 and 2 show that the injector assembly 1 can have an adapter 17 which is designed to be coupled to a plunger in which a stamp is mounted in a longitudinally displaceable manner. It is conceivable that an ophthalmosurgical injector is produced by coupling the injector assembly 1 to the plunger by means of the adapter 17. The ophthalmosurgical injector thus has the injector assembly 1, the plunger and the stamp. The stamp can be designed to be inserted into the folding chamber 8 via the adapter 17 and to push the intraocular lens 9 folded by the folding wedge 2 out of the folding chamber 8 into a cannula 14 of the injector assembly 1 and to push same from the cannula 14 out of the injector assembly 1.

Figure 5:
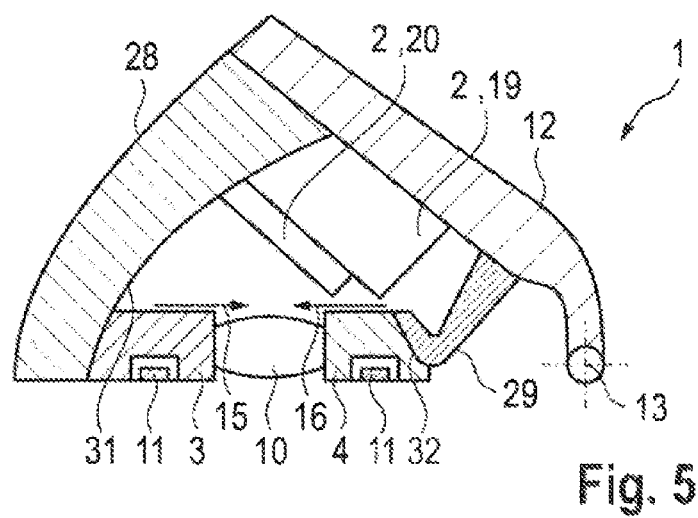
FIG. 5 shows a side view of a third embodiment of the injector assembly according to the invention with a first slider and a second slider, which are shown in a starting position.

FIGS. 1 and 5 show that the folding wedge 2 has a stationary folding wedge part 19, which is fastened to the holder 12, and a movable folding wedge part 20, which is movably attached to the stationary folding wedge part 19 and can protrude from the stationary folding wedge part 19. The stationary folding wedge part 19 can have a slot in which the movable folding wedge part 20 is arranged. The arrangement with the stationary folding wedge part 19 and the movable folding wedge part 20 can prevent the intraocular lens 9 from slipping away laterally in the direction of the holder 12 and becoming jammed.

FIGS. 1 and 2 show a first embodiment for the injector assembly 1. In the first embodiment, the injector assembly 1 has a pusher 22 which is fastened to the first slider 3 and extends from the first slider 3 toward the joint 13, wherein the holder 12 is designed to drive the pusher 22, by means of pivoting of the holder 12 about the joint 13 in the direction of the folding chamber 8, which thereby displaces the first slider 3 into the end position. In FIG. 1, the first slider is shown both in its starting position, denoted by the reference numeral 3, and in its end position, denoted by the reference numeral 3a (drawn with a dashed line). The folding wedge 2 is arranged outside the folding chamber 8. FIG. 2 shows that the holder 12 has been pivoted in the direction of the folding chamber 8 and thus the pusher 22 has been displaced in a direction away from the joint 13, as a result of which the first slider 3 has been brought into the end position. When the holder 12 is pivoted, the pusher 22 can come into contact with the holder 12 or with a component fastened to the holder 12, but without being fastened to the holder 12 or to the component. In order to fasten the pusher 22 to the first slider 3, the first slider 3 can have a slider protrusion 25 protruding from a side of the first slider 3 facing away from the second slider 4. The pusher 22 can have a first pusher pin 23 and a second pusher pin 24 between which the slider protrusion 25 is clamped.

Figure 3:
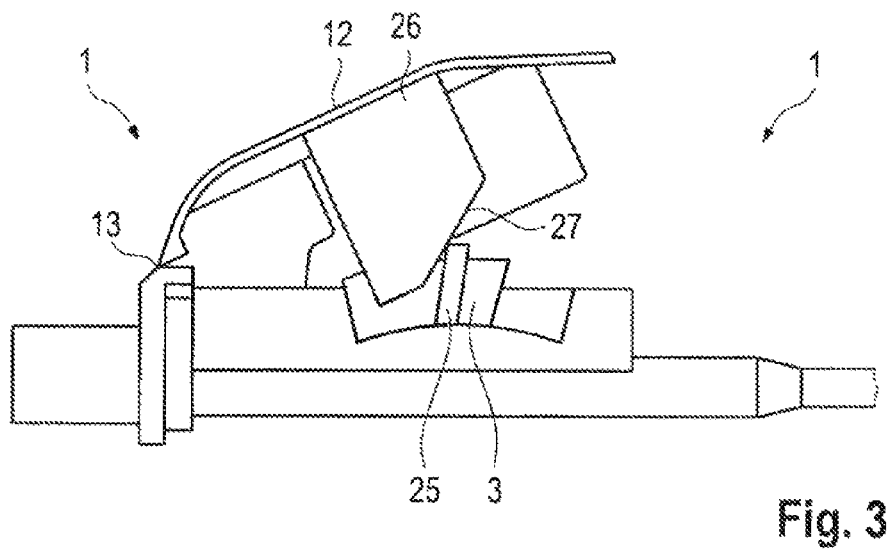
FIG. 3 shows a side view of a second embodiment of the injector assembly according to the invention with a first slider, which is shown in a starting position.
Figure 4:
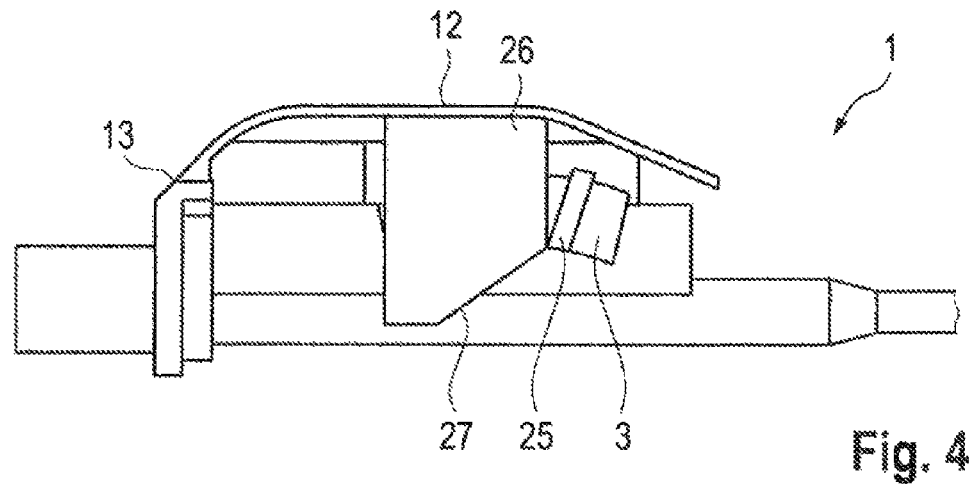
FIG. 4 shows a side view of the second embodiment with the first slider, which is shown in an end position.

FIGS. 3 and 4 show a second embodiment of the injector assembly 1. In the second embodiment, the injector assembly 1 has a first protrusion 26 fastened to the holder 12 with a first sliding surface 27 which is designed to slide along the first slider 3, when the holder 12 is pivoted about the joint 13 in the direction toward the folding chamber 8, and thereby to displace the first slider 3 into the end position. The first slider 3 has a first slider protrusion 25 protruding from a side of the first slider 3 facing away from the second slider 4 and on which the first sliding surface 27 is designed to slide. The first sliding surface 27 is in the form of a plane. Alternatively, it is conceivable that the first sliding surface 27 is curved. It is conceivable here that the first sliding surface 27 is convex if the first sliding surface 27 is designed to displace the first slider 3 away from the joint 13, and is designed concavely if the first sliding surface 27 is designed to displace the first slider 3 toward the joint 13. This allows the first slider surface 27 to slide on the first slider 3 easily.

It is also conceivable that the injector assembly 1 has a second protrusion which is fastened to the holder 12 and has a second sliding surface which is designed to slide along the second slider 4, when the holder 12 is pivoted about the joint 13 in the direction of the folding chamber 8, and thereby to displace the second slider 4 into the end position. In this case, the second slider 4 has a second slider protrusion which protrudes from a side of the second slider 4 which faces away from the first slider 3 and on which the second sliding surface is designed to slide. The second sliding surface can be in the form of a plane or can be curved. When the second sliding surface is curved, it is conceivable that the first sliding surface 27 is convex if the second sliding surface is designed to displace the second slider 4 away from the joint 13, and is designed concavely if the second sliding surface is designed to displace the second slider 4 toward the joint 13. This allows the second slider surface to slide on the second slider 4 easily.

FIG. 5 shows a third embodiment of the injector assembly 1. In the third embodiment, the injector assembly has a first protrusion 28 fastened to the holder 12 with a first sliding surface 31 which is designed to slide along the first slider 3, when the holder 12 is pivoted about the joint 13 in the direction toward the folding chamber 8, and thereby to displace the first slider 3 into the end position. The first sliding surface 31 can be designed to contact a side of the first slider 3 which faces away from the joint 13 when the holder 12 is pivoted and thereby to displace the first slider 3 in a first movement direction 15 in the direction of the joint 13. In addition, it is conceivable that the first sliding surface 31 is curved and, in particular, concave.

In addition, it is conceivable that the injector assembly 1 has a second protrusion 29 which is fastened to the holder 12 and has a second sliding surface 32 which is designed to slide along the second slider 4, when the holder 12 is pivoted about the joint 13 in the direction of the folding chamber 8, and thereby to displace the second slider 4 into the end position. The second sliding surface 32 can be designed to contact a side of the second slider 4 which faces away from the joint 13 when the holder 12 is pivoted and thereby to displace the second slider 4 in a second movement direction 16 away from the joint 13. In addition, it is conceivable that the second sliding surface 32 is curved and, in particular, convex.

FIG. 6 shows a fourth embodiment of the injector assembly 1. In the fourth embodiment, the injector assembly 1 has a wheel 35 which is designed to displace the first slider 3 from the starting position into the end position by rotation of the wheel 35, and the holder 12 is designed to set the wheel 35 in rotation by means of pivoting the holder 12 about the joint 13 toward the folding chamber 8. In addition, the wheel can be designed to displace the second slider 4 from the starting position into the end position as a result of the rotation.

It is conceivable that the injector assembly 1 has a first rod 36, by means of which the wheel 35 is coupled to the first slider 3 to drive the first slider 3, and has a second rod 37, by means of which the wheel 35 is coupled to the second slider 4 to drive the second slider 4. The first rod 36 can be articulated at its first longitudinal end by means of a first wheel joint 42 on a side surface of the wheel 35 and the second rod 37 can be articulated at its second longitudinal end by means of a second wheel joint 43 on the side surface of the wheel 35, as is also shown in FIG. 6. The first wheel joint 42 and the second wheel joint 43 can be attached here to a position of the wheel where they are symmetrical to each other with respect to the axis of rotation 46 of the wheel 35. The effect achieved by this is that either the first rod 36 is loaded under tension and the second rod 37 is loaded under compression, or the first rod 36 is loaded under compression and the second rod 37 is loaded under tension.

It can also be seen in FIG. 6 that it is conceivable for the injector assembly 1 to have a third rod 38 which is coupled at its first longitudinal end by means of a first coupling joint 44 to the second longitudinal end of the first rod 36. The second longitudinal end of the third rod 38 is coupled to the first slider 3 by means of a first slider joint 40. It can also be seen that it is conceivable for the injector assembly 1 to have a fourth rod 39 which is coupled at its first longitudinal end by means of a second coupling joint 45 to the second longitudinal end of the second rod 37. The second longitudinal end of the fourth rod 39 is coupled to the second slider 4 by means of a second slider joint 41. The first coupling joint 44 and/or the second coupling joint 45 here can have limited freedom of movement such that the first coupling joint 44 and/or the second coupling joint 45 can only move away from the injector body 7 to a limited extent.

As an alternative to providing the third rod 38 and the fourth rod 39, it is conceivable that the second longitudinal end of the first rod 36 is coupled to the first slider 3 by means of a first slider joint 40 and the second longitudinal end of the second rod 37 is coupled to the second slider 4 by means of a second slider joint 41.

FIG. 6 also shows that the joint 13 can have a pin 33 which rotates when the holder 12 is pivoted and to which a first gearwheel 34 is fastened, and the wheel 35 is a second gearwheel 35, the teeth of which mesh with the teeth of the first gearwheel 34, for example by means of a bevel gear. As a result, when the holder 12 is pivoted, the first gearwheel 34 rotates, which in turn drives the second gearwheel 35. The axis of rotation of the first gearwheel 34 and the axis of rotation of the pin 33 can coincide. In addition, the axis of rotation of the first gearwheel 34 and the axis of rotation of the second gearwheel 35 can be arranged substantially perpendicular to each other.

LIST OF REFERENCE SIGNS

1 injector assembly
2 folding wedge
3 first slider
4 second slider
5 first slider track
7 injector body
8 folding chamber
9 intraocular lens
10 optics body
11 haptics 12 holder
13 joint
14 cannula
15 first movement direction
16 second movement direction
17 adapter
18 folding chamber opening
19 stationary folding wedge part
20 movable folding wedge part
21 slider pin
22 pusher
23 first pusher pin
24 second pusher pin
25 slider protrusion
26 first protrusion
27 first sliding surface
28 first protrusion
29 second protrusion
31 first sliding surface
32 second sliding surface
33 pin
34 first gearwheel
35 wheel, second gearwheel
36 first rod
37 second rod
38 third rod
39 fourth rod
40 first slider joint
41 second slider joint
42 first gearwheel joint
43 second gearwheel joint
44 first coupling joint
45 second coupling joint
46 axis of rotation

The invention claimed is:

1. An injector assembly having a folding chamber which is designed to accommodate an intraocular lens comprising an optics body and two haptics, a holder, a folding wedge, which is attached to the holder and is designed to be introduced into the folding chamber via a folding chamber opening and thereby to fold the intraocular lens, and a first slider and a second slider which are each designed to displace one of the two haptics onto the optics body by displacement of the respective slider from a starting position into an end position, wherein the holder is designed to drive the first slider and/or the second slider from the starting position into the end position by movement of the holder toward the folding chamber, wherein the injector assembly has an injector body, inside which the folding chamber is arranged, and a joint by means of which the holder is attached pivotably to the injector body.

2. The injector assembly as claimed in claim 1, wherein the injector assembly has a pusher which is fastened to the first slider and extends from the first slider toward the joint, wherein the holder is designed to drive the pusher, by means of pivoting of the holder about the joint in the direction of the folding chamber, which thereby displaces the first slider into the end position.

3. The injector assembly as claimed in claim 1, wherein the injector assembly has a first protrusion which is fastened to the holder and has a first sliding surface which is designed to slide along the first slider, when the holder is pivoted about the joint in the direction of the folding chamber, and thereby to displace the first slider into the end position.

4. The injector assembly as claimed in claim 3, wherein the first slider has a first slider protrusion which protrudes from a side of the first slider facing away from the second slider and on which the first sliding surface is designed to slide, and/or wherein the second slider has a second slider protrusion which protrudes from a side of the second slider facing away from the first slider and on which the second sliding surface is designed to slide.

5. The injector assembly as claimed in claim 1, wherein the injector assembly has a wheel which is designed to displace the first slider from the starting position into the end position by rotation of the wheel, and the holder is designed to set the wheel in rotation by means of pivoting the holder about the joint toward the folding chamber.

6. The injector assembly as claimed in claim 5, wherein the wheel is designed to displace the second slider from the starting position into the end position as a result of the rotation.

7. The injector assembly as claimed in claim 5, wherein the injector assembly has a first rod, by means of which the wheel is coupled to the first slider to drive the first slider, and/or has a second rod, by means of which the wheel is coupled to the second slider to drive the second slider.

8. The injector assembly as claimed in claim 5, wherein the joint has a pin which rotates upon pivoting of the holder and to which a first gearwheel is fastened, and the wheel is a second gearwheel, the teeth of which mesh with the teeth of the first gearwheel.

9. An ophthalmosurgical injector having an injector assembly as claimed in claim 1.

* * * * *